(12) United States Patent
McLaughlin

(10) Patent No.: US 6,558,654 B2
(45) Date of Patent: May 6, 2003

(54) COMPOSITION AND METHOD FOR WHITENING TEETH

(76) Inventor: Gerald McLaughlin, 12 Cottonwood Ave., Port Jefferson Station, NY (US) 11776

( * ) Notice: Subject to any disclaimer, the term of this patent is extended or adjusted under 35 U.S.C. 154(b) by 0 days.

(21) Appl. No.: 09/833,012

(22) Filed: Apr. 10, 2001

(65) Prior Publication Data

US 2002/0009420 A1 Jan. 24, 2002

Related U.S. Application Data

(60) Provisional application No. 60/196,117, filed on Apr. 11, 2000.

(51) Int. Cl.[7] ............ A61K 7/20; A61K 31/78; A61K 33/40
(52) U.S. Cl. ............ 424/53; 433/215; 433/216
(58) Field of Search ............ 8/408, 409; 433/215, 433/216; 424/53

(56) References Cited

U.S. PATENT DOCUMENTS

| | | |
|---|---|---|
| 4,616,074 A | 10/1986 | Ruffner |
| 5,171,564 A | 12/1992 | Nathoo et al. |
| 5,213,789 A | 5/1993 | Degenhardt et al. |
| 5,785,527 A | 7/1998 | Jensen et al. |
| 5,840,789 A | 11/1998 | Verstrat et al. |
| 5,849,042 A * | 12/1998 | Lim et al. ............ 8/408 |
| 5,851,237 A * | 12/1998 | Anderson et al. ........ 8/409 |
| 5,865,854 A * | 2/1999 | Lim et al. ............ 8/409 |
| 5,961,666 A * | 10/1999 | Lim et al. ............ 8/408 |
| 5,993,491 A * | 11/1999 | Lim et al. ............ 8/409 |
| 6,025,431 A | 2/2000 | Cardinali et al. |
| 6,074,438 A * | 6/2000 | Lim et al. ............ 8/409 |
| 6,108,850 A | 8/2000 | McLaughlin |
| 6,190,647 B1 * | 2/2001 | Karlen et al. ........ 424/70.2 |
| 6,403,542 B1 * | 6/2002 | Maurin et al. ........ 510/122 |

FOREIGN PATENT DOCUMENTS

| | | |
|---|---|---|
| EP | 0 240 315 A2 | 10/1987 |
| EP | 0824 914 A1 | 2/1998 |
| FR | 2 773 992 | 7/1999 |
| JP | 2000247851 A2 | 9/2000 |
| WO | WO 98/30494 | 7/1998 |

OTHER PUBLICATIONS

"Structure® 2001 Acrylates/Steareth—20 Itaconate Copolymer, Structure® 3001 Acryltes/Ceteth–20 Itaconate Copolymer", National Starch & Chemical Technical Bulletin (http://www.personalcarepolymers.com/personalcare/techinfo/prodoverview/structure3001.asp, Mar. 29, 2001).
"Structure® Plus Acrylates/Aminoacrylates/C10–30 Alkyl PEG–20 Itaconate Copolymer", National Starch & Chemical Technical Bulletin (http://www.personalcarepolymers.com/personalcare/techinfo/prodoverview/structureplus.asp, Mar. 29, 2001.

* cited by examiner

*Primary Examiner*—Shep K. Rose
(74) *Attorney, Agent, or Firm*—Klarquist Sparkman, LLP

(57) ABSTRACT

A method for whitening teeth that includes contacting at least one tooth with a composition that includes a bleaching agent; a carrier; and an acrylate/$\alpha$, $\beta$-ethylenically unsaturated dicarboxylic acid or anhydride copolymer such as an acrylate itaconate copolymer. The acrylate itaconate copolymer may be an alkali-swellable polymer and the composition may further include an alkaline additive.

8 Claims, No Drawings

COMPOSITION AND METHOD FOR WHITENING TEETH

This application claims priority to U.S. Provisional Patent Application No. 60/196,117 filed Apr. 11, 2000, incorporated herein by reference.

FIELD OF THE DISCLOSURE

The present invention relates to the field of dentistry, particularly to the whitening of teeth.

BACKGROUND

Over the last decade, one of the most prominent changes in dentistry has been the increased focus in aesthetic procedures. Teeth generally become more darkly pigmented with age and exposure to such materials as tea and coffee, and it has long been a goal of dentistry to provide a means to safely and effectively reverse this darkening process. Recently, in-office and at-home teeth whitening have been rapidly embraced.

One method for whitening teeth involves using oxidizing agents to bleach the undesired pigmentation. The active agents are usually weak solutions of hydrogen peroxide or carbamide peroxide, which is more stable than hydrogen peroxide. Generally, it is believed that there are only three primary variables that can be manipulated to control the rate of whitening.

The first variable is concentration of the peroxide. In order to make the procedure occur during a reasonable time span, concentrations of peroxide equivalent to at least 3 weight percent hydrogen peroxide are employed, with the concentrations going as high as 40 weight percent. The peroxide has been used in liquid, paste and gel forms, with the gel being the most popular. The second variable is exposure time, i.e., the time the tooth is exposed to the peroxide. The third variable is the pH of the peroxide mixture.

It is well known that tooth whiteners with higher pH are more effective than equally strong whiteners with lower pH. Unfortunately, increased pH also means decreased peroxide stability. It is for this reason that none of the present tooth whitening materials have a pH much above neutral, while the majority of them are actually acidic. The only exceptions to this rule are those materials that require addition of an alkalinity adjuster immediately prior to use, but this approach has little consumer or professional appeal because of the complex handling and preparation procedures.

Another barrier to achieving a desirable tooth whitening product is the lack of a good gelling material to use at the higher pH ranges. Virtually all of the current stable tooth-whitening gels use a carbomer matrix. Carbomer in its initial gelled form has a pH around 1 to 2. As the pH is raised, the carbomer begins to lose its viscosity and stability, such that it is only with great effort and skill that it can be made to remain useful above a neutral pH. For that matter, high concentrations of peroxide are also an anathema for the carbomer since it has some tendency to oxidize with strong agents.

These two factors combine in such a way that the only single-tube high-concentration peroxide gel product known by the present inventor to ever reach the marketplace (supplied by Ultradent of Salt Lake City, Utah) is sufficiently sensitive to destabilization by heat exposure that the manufacturer refuses to ship during certain weather conditions or over a weekend. Once received by the dentist, the material has to be refrigerated at all times, or again its potency is at risk. Yet, so significant is the need for such a product that even this unstable product is successful. However, the end user is left with a product that has unpredictable and unsatisfactory characteristics since its effectiveness can be completely destroyed by a common, uncontrollable event such as a slow shipment.

Manufacturers have long sought to stabilize their hydrogen peroxide in order to extend its service life. For more than a decade, almost all the large producers of hydrogen peroxide have produced various stabilized variations of their peroxide. For instance, one such stabilized hydrogen peroxide from Degussa became available several years ago but neither the Degussa product nor any other stabilized hydrogen peroxide has been embraced by the dental community. Doubtless this is because peroxide stability is only one part of the problem with the present whitening gels, and without the other part (the gel matrix material) in place there is no advantage of using this specialty product.

Thus, a need exists for a high pH, bleaching agent-containing gel or thickened composition that is available as a stable single-package or one-part premixed product. Over the years, many gel-forming materials have been used in an attempt to make a stable high peroxide concentration, high pH gel. None of these attempts have met with any success.

SUMMARY OF THE DISCLOSURE

According to one disclosed embodiment, an improved method for whitening at least one tooth has been discovered that includes contacting the tooth with a composition that includes a bleaching agent; a carrier; and an acrylate/$\alpha$, $\beta$-ethylenically unsaturated dicarboxylic acid or anhydride copolymer. In particular embodiments the acrylate/$\alpha$, $\beta$-ethylenically unsaturated dicarboxylic acid or anhydride copolymer is an acrylate itaconate copolymer. The acrylate/$\alpha$, $\beta$-ethylenically unsaturated dicarboxylic acid or anhydride copolymer (e.g., acrylate itaconate copolymer) serves as a rheology modifier that contributes unique characteristics to the whitening method and composition. In particular, the rheology modifier allows for the formulation of a stable high pH whitening gel or thickened composition that can be provided to the user in the form of a single-package or one-part premixed product.

The acrylate itaconate copolymer may be an alkali-swellable polymer that provides thickening to a composition when the pH of the composition is increased. Thus, according to a further disclosed embodiment there is provided a composition useful for whitening teeth that includes a bleaching agent; a carrier; an alkaline additive; and an acrylate itaconate copolymer.

According to one variant the rheology modifier can be prepared by polymerizing at least one (meth)acrylate or (meth)acrylic acid monomer with a surfactant monomer, the surfactant monomer being an esterification product of a nonionic surfactant reacted with itaconic acid. According to another variant the rheology modifier can be prepared by polymerizing (a) an acrylate monomer selected from a $C_1$–$C_6$ alkyl ester of acrylic acid and a $C_1$–$C_6$ alkyl ester of methacrylic acid; (b) a monomer selected from a vinyl-substituted heterocyclic compound containing at least one of a nitrogen or a sulfur atom, a (meth)acrylamide, a mono- or di-($C_1$–$C_4$)alkylamino ($C_1$–$C_4$)alkyl (meth)acrylate and a mono or di-($C_1$–$C_4$)alkylamino ($C_1$–$C_4$)alkyl (meth)acrylamide; and (c) a surfactant monomer.

The foregoing features and advantages will be come more apparent from the following detailed description of several embodiments.

DETAILED DESCRIPTION OF SEVERAL EMBODIMENTS

The bleaching agent is any material that has the ability to whiten teeth. Illustrative bleaching agents include an oxygen radical or hydrogen radical-generating compound such as metal ion free peroxides, organic peroxides, and metal ion containing peroxides. Specific, non-limiting examples of bleaching agents include carbamide peroxide, carbamyl peroxide, calcium peroxide, sodium percarbonate, perhydrol urea, urea peroxide, sodium perborate, calcium hydroxide, potassium chlorate, magnesium carbonate, hydrogen peroxide, materials that produce these compounds in situ, and combinations thereof.

The amount of bleaching agent in the composition may vary. For example, the bleaching agent could be present in an amount of about 3 to about 60 weight percent, based on the total amount of the bleaching agent and the carrier. If hydrogen peroxide is the bleaching agent, according to one particular embodiment, it may be present in about 3 to about 40 weight percent, especially about 7 to about 15 weight percent, based on the total amount of hydrogen peroxide and the carrier. If carbamide peroxide is the bleaching agent, according to one particular embodiment, it may be present in about 10 to about 60 weight percent, based on the total amount of hydrogen peroxide and the carrier. When using embodiments with a higher amount of bleaching agent (for example, about 30 to about 50 weight percent), a rubber dam may be used to isolate the composition from the more delicate soft tissues. The composition may be subjected to a light or other source of radiant (heat) energy such as the VIRTUOSO LIGHT (commercially available from Den Mat of San Mateo, Calif.) to increase the whitening activity of the composition. Typically, the radiant energy is applied while the composition is in contact with the tooth.

The bleaching agent may be provided in a stabilizer vehicle that is mixed into the disclosed composition embodiments. For example, such stabilized bleaching agent may be aqueous or non-aqueous and include glycerin, polyethylene glycol, and similar water miscible or water immiscible organic solvents. Stabilized bleaching agent formulations may also include thickening or gelling agents such as polyoxyethylene/polyoxypropylene block copolymers or carbomer polymers. Stabilized bleaching agents are commercially available such as, for example, under the trade designation PERALKYLI from Degussa.

A polymeric rheology modifier or thickener is an additional ingredient of the composition. The rheology modifier may be an acrylate/α, β-ethylenically unsaturated dicarboxylic acid or anhydride copolymer made by copolymerizing at least one (meth)acrylate or (meth)acrylic acid monomer with a surfactant monomer as described in U.S. Pat. No. 4,616,074, the entirety of which is incorporated herein by reference. As used herein, (meth)acrylate refers to methacrylate or acrylate monomers and (meth)acrylic acid refers to methacrylic acid or acrylic acid monomers. The surfactant monomer may be made by esterifying a nonionic surfactant with an α, β-ethylenically unsaturated dicarboxylic acid monomer The α, β-ethylenically unsaturated dicarboxylic acid monomer may have a chemical structure represented by:

$$RCH=C(R_1)-COOH$$

wherein R is H or a $C_1-C_6$ alkyl group and $R_1$ is $-R_2COOH$ (wherein $R_2$ is a $C_1-C_6$ divalent alkylene), or $-COOX$ (wherein X is H or a $C_1-C_6$ alkyl group), or R is $-COOX$ (wherein X is H or a $C_1-C_6$ alkyl group) and $R_1$ is H or a $C_1-C_6$ alkyl group. Illustrative α, β-ethylenically unsaturated dicarboxylic acid or anhydride monomers include fumaric, maleic and itaconic acid (also known as methylene succinic acid) or anhydride.

Examples of nonionic surfactants that can be esterified with α, β-ethylenically unsaturated dicarboxylic acid or anhydride monomers are the polyoxyethylene alcohols such as poly(oxyethylene)$_{20}$ stearyl ether, poly(oxyethylene)$_{20}$ cetyl ether and poly(oxyethylene)lauryl ether; ethoxylated alkyl phenols such as poly(oxyethylene)$_3$ nonylphenol and poly(oxyethylene)$_8$ dinonyl phenol; polyoxyethylene fatty acid esters such as poly(oxyethylene)$_8$ stearate and poly(oxyethylene)$_{40}$ stearate; sorbitan fatty acid esters such as sorbitan monooleate and sorbitan monostearate; and polyoxyethylene sorbitan fatty acid esters, such as poly(oxyethylene)$_{20}$ sorbitan monolaurate and poly(oxyethylene)$_{40}$ monostearate.

Illustrative (meth)acrylate monomers include $C_1-C_8$ alkyl esters and $C_1-C_8$ hydroalkyl esters of (meth)acrylic acid such as methyl acrylate, ethyl acrylate, butyl acrylate, 2-ethyl hexyl acrylate, methyl methacrylate, ethyl methacrylate, butyl methacrylate, 2-hydroxybutyl acrylate, 2-hydroxyethyl methacrylate and 2-hydroxypropyl methacrylate.

The acrylate/α, β-ethylenically unsaturated dicarboxylic acid or anhydride copolymer may be prepared by emulsion copolymerization at low pH (e.g., 2.5–5) as described in U.S. Pat. No. 4,616,074. As described in more detail below, the resulting aqueous emulsion thickens upon raising of the pH.

According to particular embodiments of the composition, an acrylate itaconate copolymer may serve as the rheology modifier. Illustrative acrylate itaconate copolymers include an acrylate/steareth-20 itaconate copolymer or an acrylate/ceteth-20 itaconate copolymer. Such acrylate itaconate rheology modifiers are commercially available from National Starch and Chemical, Bridgewater, N.J., under the trade designation STRUCTURE® 3001 (an acrylate/ceteth-20 itaconate copolymer) and STRUCTURE® 2001 (an acrylate/steareth-20 itaconate copolymer). These acrylate itaconate copolymers are said to have a chemical structure represented by:

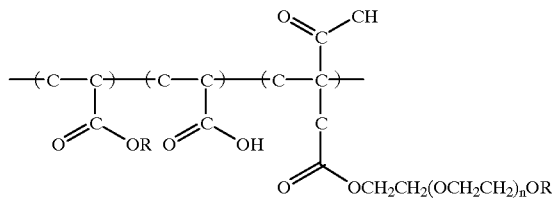

wherein R can be a $C_1-C_8$ alkyl or hydroxyalkyl and n can be an integer from 1 to 40.

According to an alternative embodiment, the rheology modifier may be a polymeric rheology modifier as described, for example, in U.S. Pat. No. 5,840,789 and EP-A-0 824 914. In a particular embodiment, the rheology modifier may be an aqueous emulsion of a (meth)acrylic polymer prepared by emulsion polymerization of at least three monomers—an acrylate monomer (a), an amine monomer (b) and a surfactant monomer (c) as described above. Such polymeric rheology modifiers are commercially available from National Starch and Chemical, Bridgewater, N.J., under the trade designation STRUCTURE® PLUS (an acrylate/aminoacrylate/$C_{10}-C_{30}$ alkyl polyethylene glycol-20 itaconate copolymer).

According to U.S. Pat. No. 5,840,789 and EP-A-0 824 914, the acrylate monomers (a) are selected from esters prepared from (meth)acrylic acid and $C_1$–$C_6$ alcohols, such as ethyl or propyl alcohol. Illustrative acrylate monomers include $C_2$–$C_6$ alkyl esters of acrylic acid such as, for example, ethyl acrylate. According to EP-A-0 824 914 and U.S. Pat. No. 5,840,789, methyl acrylate should not be used in preparing the rheology modifier emulsions disclosed therein where stable emulsions are required since it is said to result in emulsions that are unstable with respect to viscosity change over time.

In addition to the acrylate monomer (a), polymerized therewith is a monomer (b) selected from a vinyl-substituted heterocyclic compound containing at least one of a nitrogen or sulfur atom, a (meth)acrylamide, a mono- or di-($C_1$–$C_4$) alkylamino ($C_1$–$C_4$)alkyl (meth)acrylate, or a mono or di-($C_1$–$C_4$)alkylamino ($C_1$–$C_4$)alkyl (meth)acrylamide. Exemplary monomers include N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide and N,N-diethylamino propyl methacrylamide.

Monomers that provide cross-linking in the acrylate itaconate copolymer may also be utilized in relatively low amounts, up to about 3 weight percent, based on the total weight of monomers. Cross-linking monomers include multi-vinyl-substituted aromatic monomers, alicyclic monomers selected from the group consisting of cycloparrafins and cycloolefins, di-functional esters of phthalic acid, di-functional esters of methacrylic acid, multi-functional esters of acrylic acid, dienes, trienes, tetraenes, and N-methylene-bis-acrylamide. Exemplary cross-linking monomers include divinylbenzene, trivinylbenzene, 1,2,4-tricinylcyclohexane, 1,5-hexadiene, 1,5,9-decatriene, 1,9-decadiene, and 1,5-heptadiene, di-allyl phthalate, ethylene glycol dimethacrylate, polyethylene glycol dimethacrylate, penta- and tetra-acrylates, and N-methylene-bis-acrylamide.

The acrylate itaconate copolymers may be prepared by known emulsion polymerization techniques such as those described in U.S. Pat. Nos. 4,616,074, 5,840,789 and EP-A-0 824 914.

The carrier component may be any material that is capable of providing a vehicle for combining and delivering the other ingredients of the disclosed compositions. Typically, the carrier is a solvent or suspending medium for the other ingredients such as water or an organic solvent. Illustrative organic carriers include glycerin, polyalkylene glycol or alcohol (e.g., polyethylene glycol or polypropylene glycol) or similar materials. According to certain embodiments, any of the ingredients may be pre-mixed with the carrier and then subsequently formulated with the remaining ingredients to produce the end-use composition. For example, the bleaching agent may be dissolved or dispersed in a carrier. In this case, water could be used as the carrier for hydrogen peroxide or glycerin or polyethylene glycol could be used as the carrier to dissolve a solid peroxide or peroxide-generator such as carbamide peroxide, calcium peroxide or sodium percarbonate. The thickening agent or rheology modifier also may be dissolved or dispersed in a carrier prior to final formulation. The amount of carrier is not critical and may be varied depending on the desired properties and characteristics.

The compositions may be formulated to have a range of viscosities depending on the desired end use. For example, the end-use composition may be a slightly thickened liquid, loosely structured gel or a thick and highly sticky viscous mass. According to a further variant, an inert gas may be mixed into the composition to produce a foam.

The desired viscosity may be achieved by any known method. One example is by varying the ratio of the rheology modifier to the other ingredients. The relative amount of rheology modifier is directly proportional to the resulting viscosity. Other optional thickeners could also be added such as carbomer, aluminum silica, carboxymethyl cellulose, hydroxyethyl cellulose, agar and other known thickeners. The higher viscosities are especially useful with stock dental trays, toothbrushes or similar devices. The lower viscosities are especially useful for custom dental trays or for syringe delivery. A sprayable composition may also be formulated.

Another alternative for viscosity control is manipulating the pH of the composition. As described above, according to certain embodiments the rheology modifier is a polymer that swells in response to a change in pH. According to a particular embodiment, the rheology modifier is an alkali-swellable polymer such as, for example, the above-mentioned STRUCTURE® 3001 or STRUCTURE® 2001. According to an alternative embodiment, the rheology modifier may be a polymer that thickens in a neutral or acidic environment such as, for example, the above-mentioned STRUCTURE® PLUS. When such alkali-swellable polymers are exposed to a neutral or alkaline pH they undergo thickening, thus contributing to the increase in viscosity in the disclosed compositions. At low pH, the rheology modifier remains in its low viscosity state. For example, in the case of STRUCTURE® 3001 or STRUCTURE® 2001, the rheology modifier exists as an aqueous emulsion or latex at low pH such as, for example, about 2 to about 4. The pH of the end-use compositions may be adjusted accordingly so as to induce the desired thickening caused by the rheology modifier. For example, the pH of the end-use compositions may range from about 6.5 to about 11, more particularly from about 8 to about 10.

The pH may be controlled by any means. One example is by adding an alkaline additive to the composition. The alkaline additive can be capable of increasing the pH to at least about 6, more particularly to a pH of at least about 8. Illustrative alkaline additives include alkali metal hydroxide (e.g., sodium hydroxide), tris(hydroxymethyl) aminomethane, sodium carbonate, ammonium hydroxide, alkylamine (e.g., methylamine or dimethylamine), and amino alcohols (e.g., amino methyl propanol). The amount of alkaline additive added should be sufficient to increase the pH to its desired level.

The alkaline additive may be added during any stage of the composition manufacture. Advantageously, the alkaline additive can be added along with the other ingredients to provide a pre-mixed product that can be provided to the end user. In other words, there is no need to add the alkaline additive immediately prior to use, thus avoiding the mixing drawbacks associated with two-part systems. However, if desired, a two-part system can be provided that includes the rheology modifier in one part and the alkaline additive in the second part.

The pH of the end-use composition may also be adjusted by mixing an additional ingredient into a formulated composition that already includes the bleaching agent, rheology modifier, alkaline additive and carrier (referred to herein as an "intermediate stage composition"). If the pH of the additional ingredient is greater than the pH of the intermediate stage composition, the composition will thicken further. If the pH of the additional ingredient is less than the pH of the intermediate stage composition, the viscosity of the composition will decrease due to irreversible breakage of physical associations created by the rheology modifier. Once the viscosity is decreased in this manner, the composition cannot subsequently undergo re-thickening by raising the pH. If the pH of the additional ingredient is about equal to the pH of the intermediate stage composition, then the viscosity decreases via simple dilution. Thus, an additional advantage of the composition is that the viscosity and pH are not directly linked. In other words, a composition may be formulated to provide a particular pH and a particular viscosity over wide pH and viscosity ranges.

The additional ingredient for adding to the intermediate stage composition may be any of the ingredients disclosed herein. For example, a bleaching agent could be added to the intermediate stage composition. The intermediate stage composition could be formulated to a viscosity that is higher than desired for end use, and then thinned with a solution that contains the bleaching agent and has a pH lower than that of the intermediate stage composition.

The disclosed composition may also include a catalytic agent as described in U.S. Pat. No. 6,108,850. According to a particular embodiment, the catalytic agent accelerates the release of oxygen radicals from an oxygen radical generating bleaching agent. Examples of such catalytic agents include, but are not limited to, activated charcoal, platinum, platinum salts, copper, copper salts, palladium, palladium salts, silver, and silver salts. The composition may also include other bleaching accelerators or enhancers such as amino acids (e.g., glycine, hydroxy-proline, trytophane, arginine, etc.), iron salts, magnesium salts and similar known materials. If such a catalytic agent or accelerator is present, it typically is provided in a separate part or package that is mixed with the oxygen radical generating bleaching agent shortly before use of the composition.

Another optional ingredient in embodiments of the invention is an abrasive material. For example, a dicalcium phosphate abrasive may be incorporated into the composition (e.g., see U.S. Pat. No. 5,171,564). Examples of dicalcium phosphate abrasives include, but are not limited to dicalcium phosphate dihydrate, anhydrous dicalcium, or calcium pyrophosphate. Other possible abrasives include siliceous materials. Examples of such materials include, but are not limited to, silica abrasives, such as precipitated amorphous hydrated silica, and alumina abrasives, such as alumina trihydrate, aluminum silicate, calcined alumina, and bentonite.

The abrasive material may be included in a carrier vehicle that may contain water, humectant, surfactant, and a thickener. Examples of humectants are glycerin, sorbitol, and polyethylene glycol (molecular weight 200–1000) and mixtures thereof. Thickeners may be incorporated in the abrasive component such as natural and synthetic gums such as carrageenan, xanthan gum, sodium carboxymethyl cellulose, starch, polyvinylpyrrolidone, hydroxyethylpropyl cellulose, hydroxybutyl methyl cellulose, hydroxypropyl methyl cellulose, and hydroxyethyl cellulose.

In another embodiment, an agent for administering fluoride, such as a fluorine providing salt, which has activity against cavities, may be incorporated into the composition. Such materials are characterized by their ability to release fluoride ions in water. Agents for administering fluoride include, but are not limited to, inorganic metal salts such as sodium fluoride, potassium fluoride, and tin fluoride such as stannous fluoride or stannous chlorofluoride, sodium fluorosilicate, ammonium fluorosilicate, and sodium monofluorophosphate.

According to a further embodiment, the composition may also include palliative ingredients for periodontal tissues. Examples of such ingredients include, but are not limited to, aloe, eugenol, and vitamin E. Pigments, sweeteners, colors, and flavors may also be incorporated into the composition. The composition may further include an ingredient to decrease tooth sensitivity, such as potassium nitrate.

The disclosed compositions may be placed in contact with a tooth or teeth via known techniques. One example of a method for applying the composition to teeth is via a dental tray. Such dental trays are shaped to fit into a patient's mouth and hold the composition against the teeth to be whitened. The composition can be applied on a contact surface of the tray prior to placing the tray into the patient's mouth. Alternatively, the tray can be initially placed in the patient's mouth and then the composition can be placed or injected (e.g., via a syringe or squeeze bottle) into a void between the contact surface of the tray the teeth. The dental tray can be either stock (i.e., pre-fabricated) or customized. In order to produce a customized dental tray, a sheet of moldable plastic is used that will conform to a mold of an individual's teeth. Production of such trays is well known in the art.

Another embodiment for applying the composition involves delivery via a syringe. For example, a first part containing bleaching agent, rheology modifier, an alkaline additive and a carrier can be provided in a first barrel of a two-barreled syringe and a second part containing rheology modifier, a carrier, an alkaline additive and a bleaching accelerator can be provided in the second barrel. The two parts mix as they exit the syringe through a series of baffles.

The ingredients of the composition may be combined by any known means. For example, the ingredients may be mixed together under ambient atmospheric conditions. In certain embodiments, rapid mixing accelerates the formation of a thickened composition as well as incorporates a significant number of bubbles. Depending upon the viscosity of the composition, these bubbles may rise to the surface within about 48 hours. The use of a vacuum during mixing may assist in limiting the inclusion of bubbles into the composition.

The ingredients of the composition may be combined together in any order. According to a particular embodiment, the rheology modifier can be mixed with a carrier (with or without the bleaching agent) prior to the addition of the alkaline additive. According to another particular embodiment, a bleaching agent may first be diluted with water and then the rheology modifier is mixed-in at room temperature. The alkaline additive is subsequently added to the bleaching agent/rheology modifier mixture. According to a further particular embodiment, the alkaline additive may be first dissolved in a carrier prior to its addition to the end-use composition.

The specific examples described below are for illustrative purposes and should not be considered as limiting the scope of this invention.

EXAMPLE 1

Stabilized hydrogen peroxide (35% aqueous solution commercially available from Degussa under the trade designation PERALKYLI) (1.5 mL) was mixed with 4.4 mL of water. Twenty drops of STRUCTURE® 3001 rheology modifier were subsequently stirred into the mixture. Twenty drops of sodium hydroxide solution (2.5 g NaOH in 50 mL of water) then were stirred into the mixture, initiating thickening of the mixture. The resulting mixture was capable of remaining in a dental tray when the tray was inverted.

EXAMPLE 2

Example 1 was repeated except that 0.5 mL of glycerin was substituted for 0.5 mL of water.

EXAMPLE 3

Example 1 was repeated except that an aqueous solution of tris(hydroxymethyl)aminomethane was substituted for the sodium hydroxide solution.

When the compositions of Examples 1–3 were painted on stained, extracted human teeth, a visible improvement in whitening occurred within 40 minutes of exposure. This was observed by first splitting the tooth lengthwise, and then placing one half of the tooth in the exemplified compositions and the other half of the tooth into comparative compositions having the same formulations as in Examples 1–3 except that water was substituted for hydrogen peroxide. In addition, the compositions of Examples 1–3 were placed in a stock dental tray and were worn in a human mouth for about 40 minutes. After removal of the dental tray, the soft tissues exhibited no deleterious effects and the teeth were noticeably more white.

EXAMPLE 4

A two-part system was prepared by mixing together the following ingredients:
Part A
   3.0 mL stabilized hydrogen peroxide (35% aqueous solution)
   3.2 mL water
   20 drops STRUCTURE® 3001 rheology modifier
   15 drops sodium hydroxide solution (2.5 g NaOH in 50 mL water)
Part B
   6.0 mL water
   15 drops STRUCTURE® 3001 rheology modifier
   20 drops sodium hydroxide solution (2.5 g NaOH in 50 mL water)
   1.5 g magnesium gluconate (peroxide accelerator)

When parts A and B were combined and painted on the surface of stained, extracted human teeth, a visible increase in whiteness of the tooth was evident after 30 minutes. This was observed by first splitting the tooth lengthwise, and then placing one half of the tooth in the exemplified composition and the other half of the tooth into a comparative composition having the same formulation as in the Example 4 except that water was substituted for hydrogen peroxide. In addition, the composition of Example 4 was placed in a stock dental tray that was worn in a human mouth for about 30 minutes. After removal of the dental tray, the soft tissues exhibited no deleterious effects and the teeth were noticeably more white.

EXAMPLE 5

A composition utilizing carbamide peroxide rather than hydrogen peroxide was prepared by mixing together 5 mL glycerin, carbamide peroxide (in an amount sufficient to produce a final peroxide concentration of 15%), 20 drops STRUCTURE® 3001 rheology modifier, and 15 drops tris(hydroxymethyl)aminomethane. The resulting composition was a thick gel. When the composition of Example 5 was painted on stained, extracted human teeth, a visible improvement in whitening occurred within 40 minutes of exposure.

Having illustrated and described the principles of our invention with reference to several preferred embodiments, it should be apparent to those of ordinary skill in the art that the invention may be modified in arrangement and detail without departing from such principles.

I claim:

1. A single-package system for whitening at least one tooth comprising a pre-mixed composition that includes:
   (a) about 7 to about 40 weight percent bleaching agent;
   (b) a carrier;
   (c) an alkaline additive selected from alkali metal hydroxide, tris(hydroxymethyl)aminomethane, sodium carbonate, ammonium hydroxide, alkylamine or amino alcohol; and
   (d) an acrylate/$\alpha$, $\beta$-ethylenically unsaturated dicarboxylic acid or anhydride copolymer wherein the weight percent is based on the total amount of carrier and bleaching agent.

2. A system according to claim 1 wherein the bleaching agent is selected from hydrogen peroxide or carbamide peroxide.

3. A system according to claim 1 wherein the acrylate/$\alpha$, $\beta$-ethylenically unsaturated dicarboxylic acid or anhydride copolymer comprises an acrylate itaconate copolymer.

4. A system according to claim 3 wherein the acrylate itaconate copolymer is selected from an acrylate/steareth-20 itaconate copolymer, an acrylate/ceteth-20 itaconate copolymer or an acrylate/aminoacrylate/$C_{10}$–$C_{30}$ alkyl polyethylene glycol-20 itaconate copolymer.

5. A system according to claim 4 wherein the acrylate itaconate copolymer comprises an acrylate/ceteth-20 itaconate copolymer.

6. A single-package system for whitening at least one tooth comprising a pre-mixed composition that includes the combination of the following ingredients:
   (a) about 7 to about 40 weight percent bleaching agent;
   (b) a carrier;
   (c) an alkaline additive selected from alkali metal hydroxide, tris(hydroxymethyl)aminomethane, sodium carbonate, ammonium hydroxide, alkylamine or amino alcohol; and
   (d) an acrylate itaconate copolymer
wherein the weight percent is based on the total amount of carrier and bleaching agent.

7. A system according to claim 6 wherein the acrylate itaconate copolymer is selected from an acrylate/steareth-20 itaconate copolymer, an acrylate/ceteth-20 itaconate copolymer or an acrylate/aminoacrylate/$C_{10}$–$C_{30}$ alkyl polyethylene glycol-20 itaconate copolymer.

8. A two-part system for whitening at least one tooth, comprising:
   a first pre-mixed part that includes:
      (a) about 7 to about 40 weight percent bleaching agent;
      (b) a carrier;
      (c) an alkaline additive selected from alkali metal hydroxide, tris(hydroxymethyl)aminomethane, sodium carbonate, ammonium hydroxide, alkylamine or amino alcohol; and
      (d) an acrylate/$\alpha$, $\beta$-ethylenically unsaturated dicarboxylic acid or anhydride copolymer wherein the weight percent is based on the total amount of carrier and bleaching agent; and a second part that includes an accelerator.

* * * * *